United States Patent
Wood

[19]

[11] Patent Number: 5,968,075
[45] Date of Patent: Oct. 19, 1999

[54] NASAL SEPTAL BUTTON

[75] Inventor: Gordon S. Wood, Logan, Utah

[73] Assignee: Silmed, Inc., Millville, Utah

[21] Appl. No.: 09/144,151

[22] Filed: Aug. 31, 1998

[51] Int. Cl.⁶ .................................................. A61F 1/00
[52] U.S. Cl. .......................... 606/213; 606/1; 606/232; 606/198
[58] Field of Search ................................ 606/1, 213, 78, 606/151, 157, 232, 215, 108, 198

[56] References Cited

U.S. PATENT DOCUMENTS

| | | | |
|---|---|---|---|
| 4,031,569 | 6/1977 | Jacob | 606/213 |
| 4,836,204 | 6/1989 | Landymore et al. | 604/53 |
| 5,108,420 | 4/1992 | Marks | 606/213 |
| 5,192,301 | 3/1993 | Kamiya et al. | 606/213 |
| 5,334,217 | 8/1994 | Das | 606/213 |
| 5,366,478 | 11/1994 | Brinkerhoff et al. | 606/213 |
| 5,501,700 | 3/1996 | Hirata | 606/215 |
| 5,634,936 | 6/1997 | Linden et al. | 606/213 |

*Primary Examiner*—Linda C. M. Dvorak
*Assistant Examiner*—Sonya Harris-Ogugua
*Attorney, Agent, or Firm*—M. Reid Russell

[57] ABSTRACT

A medical appliance for plugging a hole in a nasal septum that includes a central member that has an irregular cross section where its major axis is longer than its minor axis and where the appliance is sized such that the length of the central portion major axis is the same or slightly shorter than a major axis of an irregularly shaped nasal septum hole, and with opposing disks secured across the opposite central member opposite ends that each have a like diameter that is greater than the length of the nasal septum hole major axis. The medical appliance is formed as a single unit from a flexible material to human body compatible material where at least one of the disks can be folded upon itself and will return to its original shape when released.

3 Claims, 4 Drawing Sheets

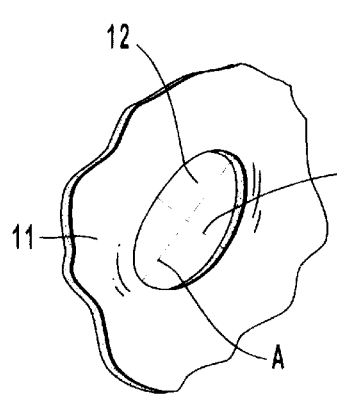
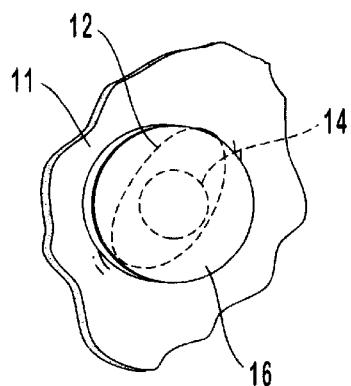
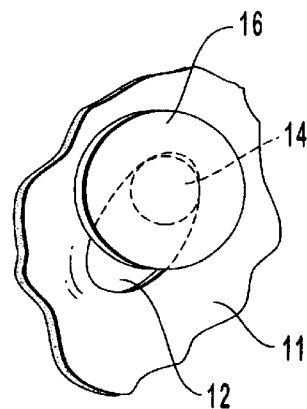
FIG. 6A
(PRIOR ART)
FIG. 6B
(PRIOR ART)
FIG. 6C
(PRIOR ART)
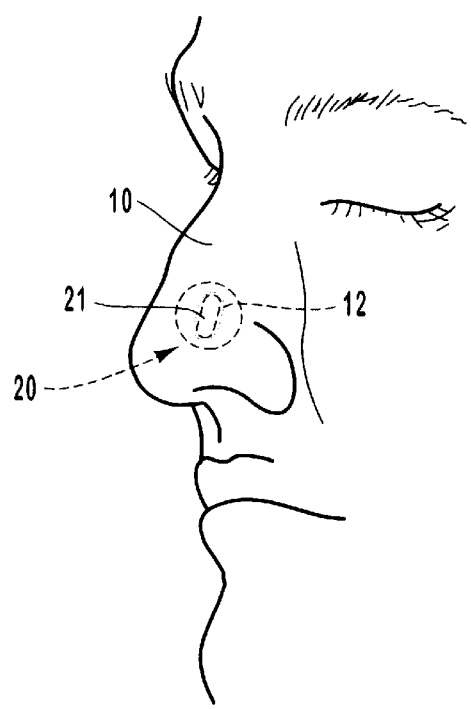
FIG. 7

NASAL SEPTAL BUTTON

BACKGROUND OF THE INVENTION

1. Field of the Invention

This invention relates to medical appliances and in particular to an appliance for use in a medical procedure for closing or "plugging" a hole in a patient's nasal septum.

2. Prior Art

The invention is a medical appliance for insertion into, so as to close off, a hole or aperture as has formed in a medical patient's nasal septum as a result of a secondary infection resulting from an infectious disease like tuberculosis; from a nasal trauma; chronic nose picking; as a result of septal surgery, or the like. Such a hole can be a round hole, but is rarely a perfect circle. Where earlier devices, such as a plug developed by H. John Jacob, U. S. Pat. No. 4,031,569, have recognized a need for a septal plug, such medical appliance has not effectively taken into account septum holes that are other than circular. In practice, therefore, such earlier plug has been used successfully for circular or nearly circular holes, such plug cylindrical member has tended to turn or move in an irregular septal hole, eroding and thus enlarging that hole, or has often been displaced to one end of the hole or the other, as in the case of a elliptical hole in the nasal septum. Accordingly, such member displacement has often opened the hole to air flow, and movement of the member across the hole has often caused hole erosion, bleeding, breathing problems and infection requiring additional medical attention.

The invention is in a utilization of a center post that is irregular in shape, preferably elliptical rather than cylindrical and axially maintains flexible disks across its ends. The irregular center post is to seat in a septum hole with its longest cross sectional axis, or major axis, fitted into a longest segment of that septum hole, and with the post minor axis fitting in the minor or shortest hole axis. So arranged, the center post cross section major and minor axis fit closely to the septum hole edge discouraging plug rotation and movement as has been common with the septum plug of the '569patent.

Additional to the '569 patent, a number of other medical appliances have been developed for closure of holes and wounds. None of such devices, however, involves a center post, or the like, that has an irregular cross section, preferably an ellipse. Examples of such earlier devices are shown in U. S. Pat. Nos. 4,836,204; 5,108,420; 5,192,301; 5,258, 000; 5,334,217; 5,366,478; 5,501,700; 5,634,936 and 5,690, 674, with the above cited '569 being the closest art to the invention.

SUMMARY OF THE INVENTION

It is a principal object of the present invention to provide an improved nasal septal button for fitting into, so as to provide an effective closure over a hole in a patient's septum, regardless of the shape of which hole.

Another object of the present invention is to provide a nasal septal button that is easily installed by a physician to fit closely in and remain positioned in a hole in a patient's septum.

Another object of the present invention is to provide a nasal septal button that will remain seated to close over a hole in a patient's septum regardless of the hole shape.

Still another object of the present invention is to provide a nasal septal button that is installed by a physician to seat, and remain stationary in covering arrangement over an irregular shaped hole in a patient's septum.

Still another object of the present invention is to provide a nasal septal button that is easily installed in a hole in a medical patient's septum that will remain essentially stationary, in covering engagement over which septal perforation.

The medical appliance of the invention is a septal button that is preferably formed as a single until from a flexible, non-toxic, non-irritating material such as a silicone that is suitable for installation in a patient's nose. The appliance consists of a straight center post having an irregular cross section, preferably an ellipse, with a greater or longer major axis than its minor axis, and with flat disk members secured across its ends. Which disk ends are each to flex freely, with one disk end to bend upon itself for fitting through a nasal septum perforation or hole and will return to its original shape after passage through which hole. So arranged, in practice, the center post major and minor axis are positioned, respectively, in the hole or perforation to align with the hole major and minor axes, and with the opposing or inner disk faces engaging, respectively, the opposite faces of the septum around the perforation or hole, closing off that perforation or hole to air passage.

Additional objects and features of the invention will become apparent from the following detailed description and claims, taken together with the accompanying drawings that show a preferred form of the invention.

THE DRAWINGS

FIG. 6A is also identified as Prior Art and shows an enlarged view of the irregularly shaped hole of FIG. 2;

FIG. 6B is also identified as Prior Art and shows the irregularly shaped hole of FIG. 6A as having received the septum nasal plug of FIGS. 3, 4 and 5 fitted therein;

FIG. 6C is also identified as Prior Art and shows the septum nasal plug of Fig. B as having moved to one end of the irregularly shaped hole of FIGS. 6A and 6B, exposing an end portion of the septum hole wherethrough an air flow can escape;

FIG. 7 is a view like that of FIG. 2 with a nasal septal button of the invention shown fitted therein, closing off the irregularly shaped septum hole;

DETAILED DESCRIPTION

Figure 1:
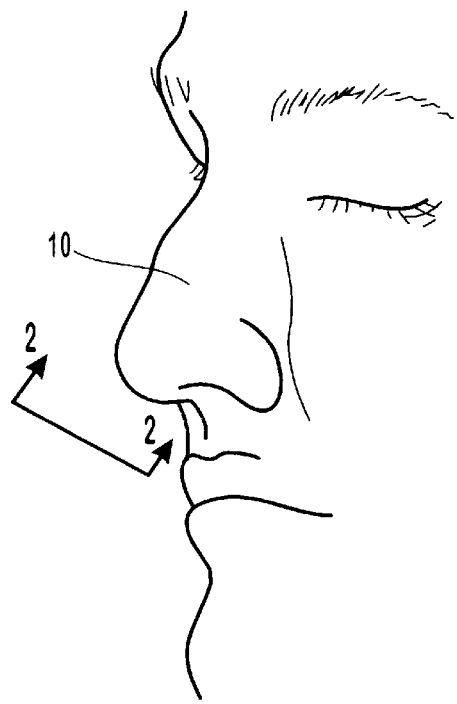
FIG. 1 is a side elevation perspective view of a medical patient's nose and their facial area therearound.
Figure 2:
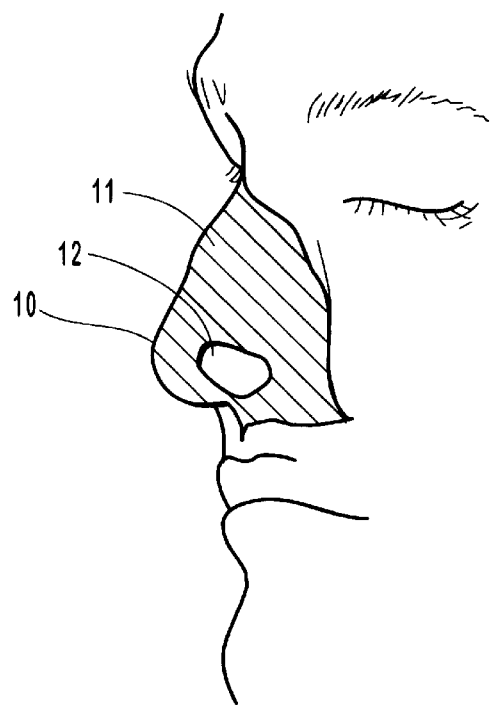
FIG. 2 is a view like that of FIG. 1 showing a section taken along the line 2—2 of the patient's nose exposing their septum that is shown as having an irregular shaped hole formed therein.

FIG. 1 shows a portion of a medical patient's face to include their face area around their nose 10. A section of the nose 10 is shown in FIG. 2 taken along the line 2—2 of FIG. 1, exposing the patient's nose septum 11 that is shown as having a hole or cavity 12 formed therein that has an irregular shape, shown in FIG. 2 as a essentially a regular ellipse, the hole or cavity shown as having a major axis that is appreciably longer than its minor axis. The hole or cavity 12 is shown as an enlarged irregular shaped hole or cavity in FIGS. 6A and 8A, as will be discussed hereinbelow with respect to a Prior Art device and a use of a nasal septal button 20 of the invention as discussed with respect to FIGS. 7 through 10. Additionally, while a regular elliptical shape is shown in FIGS. 7 through 10 as receiving the nasal septal button 20 of the invention, it should be understood that the invention can be used in any shape of hole, even one that is circular, within the scope of this disclosure.

Figure 3:
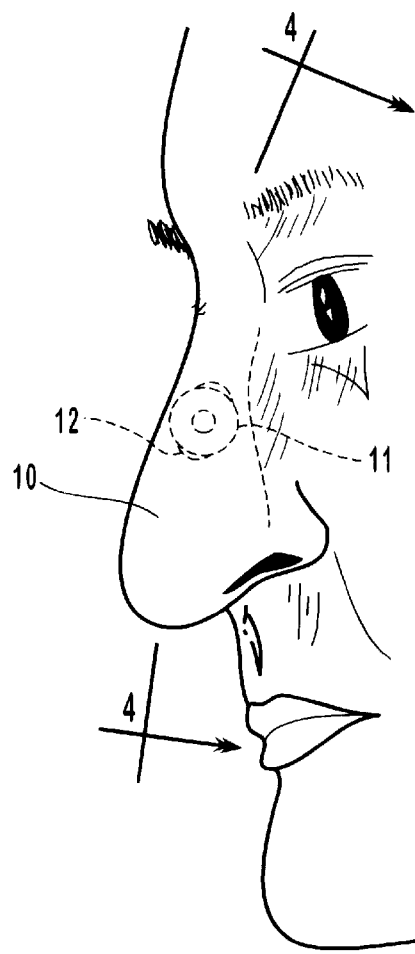
FIG. 3 is identified as Prior Art and shows a view like that of FIG. 1 of a patient's nose and showing, in broken lines, an earlier septum nasal plug installed in a septum hole or perforation.

FIG. 3, herein identified as prior art, shows an earlier embodiment of a nasal septum plug 13, shown in broken lines, that has been fitted into the irregularly shaped hole or cavity 12, shown also in broken lines, closing off a hole or cavity 12 in the patient's septum. With, in FIG. 4, that is a sectional view taken within the line 4—4 of FIG. 3 and is also identified as prior art, the nasal septum plug 13 is shown as having been removed along with the portion of the septum 11 wherein the hole or cavity 12 is formed, and the removed portions are shown enlarged. The nasal septum plug 13, it should be understood, is like that shown in the earlier cited U.S. Pat. No. 4,031,569 that the present invention improves upon.

Figure 4:
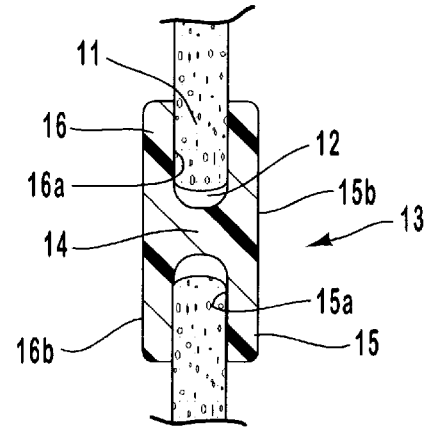
FIG. 4, is also identified as Prior Art and shows an enlarged sectional view taken along the line 4—4 of FIG. 3 of the septum nasal plug of FIG. 3.
Figure 5:
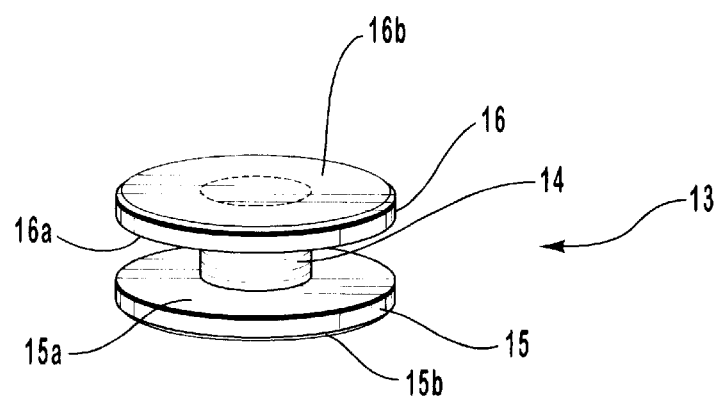
FIG. 5 is also identified as Prior Art and shows an enlarged profile prospected of the septum nasal plug of FIG. 3 after its removal from the septum hole.
Figures 8A, 8B:
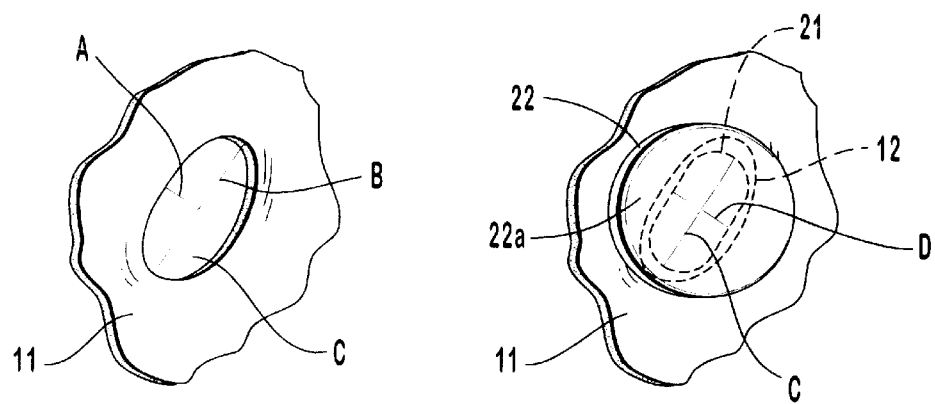
FIG. 8A is a view like that of FIG. 6A of an enlarged irregularly shaped septum hole.
FIG. 8B is a view like that of FIG. 6B only showing the nasal septal button of FIG. 7 fitted in the septum hole of FIG. 8A.

In FIG. 4, and in the profile perspective view of FIG. 5, the nasal septum plug 13 is shown to include a cylindrical center portion 14 that has a length that is substantially equal to the diameter or width of the septum 11. Disks 15 and 16 are secured across on each end of the cylindrical portion 14, and each of which disks has a diameter that is larger than the diameter of the cylindrical portion 14 and greater than the diameter of hole or cavity 12. The disks 15 and 16, as shown, are preferably flat on both inner faces 15a and 16a, respectively, and includes outer faces, 15b and 16b, respectively, that are shown as flat also, with the disks inner faces 15a and 16a to abut against the surfaces of the septum around hole or cavity 12, as shown in FIG. 4, closing off that hole or cavity. Preferably the nasal septum plug 13, like the invention, is formed from a material that is suitable for human implantation and is formed as an integral or single unit.

In practice, to install the nasal septum plug 13 into a septum hole or cavity 12, as shown in FIG. 6A, here identified as prior art, at least one of the disks 15 or 16 must be folded upon itself and fitted through the hole or cavity 12, with that folded disk to return to its original shape when released, as shown in FIG. 6B, identified as prior art. The nasal septum plug 13 fit is dependant upon the diameter of the cylindrical portion 14 that, as set out in the '569 patent, is sized to fit within the hole or cavity 12 so as to have a diameter that is equal to or slightly less than the diameter of the hole or cavity 12. Accordingly, where the hole or cavity 12 is other than circular, such as the irregular shaped hole addressed by the present invention, the controlling hole dimension will be the length of its minor axis, with the cylindrical portion 14 thereby free to travel across the hole or cavity 12, along the hole or cavity major axis, as illustrated in FIG. 6C, identified as prior art. Where, as shown in FIG. 6C, the cylindrical portion 14 has traveled to one end of the hole or cavity 12, the opposite hole or cavity end will be open, allowing an unwanted passage of air therethrough. Additionally, cylindrical portion 14 travel, along the hole or cavity 12 can erode the hole edge, providing an unwanted hole or cavity expansion, and may also cause bleeding and crusting around the hole or cavity edge perhaps resulting in infection. The present invention improves upon the nasal septum plug 13 and corrects these deficiencies.

FIG. 7 shows the patient's nose 10 as having a septum with a hole or cavity 12, shown in broken lines, formed therethrough that is closed by an installation of the nasal septal button 20 of the invention. In which installation, the elliptical central portion 21 of the nasal septal button 20, as shown in broken lines, is positioned in the septum hole or cavity such that central portion 21 major axis D is fitted along the hole or cavity 12 major axis A, and with the central portion 21 minor axis D thereby positioned along the hole or cavity minor axis B, thereby providing a close fit of the central portion 21 in the hole or cavity 12. In practice, this close fitting arrangement discourages the nasal septal button 20 from turning as could enlarge the hole or cavity or uncover a portion of that hole or cavity as has been the case utilizing the nasal septum plug 13.

Figure 9:
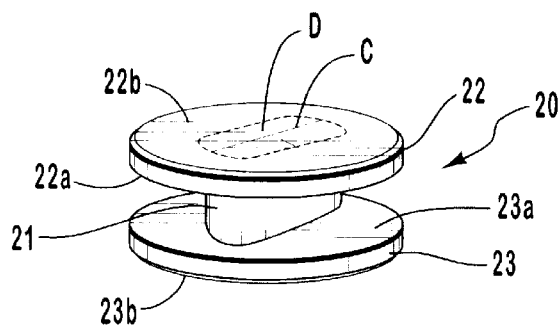
FIG. 9 is a view like that of FIG. 5 showing the nasal septal button of the invention.
Figure 10:
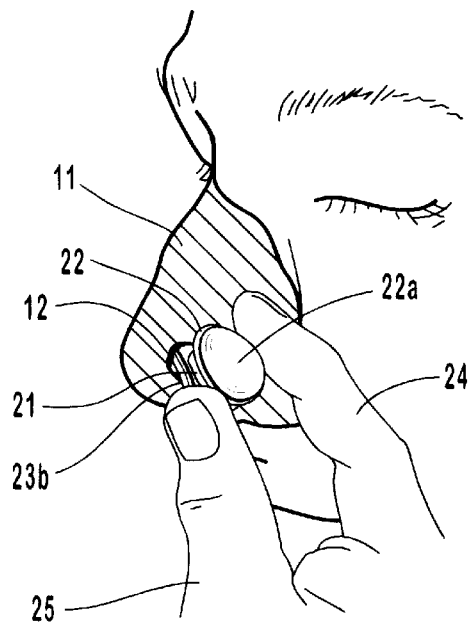
FIG. 10 is view like that of FIG. 2 showing the nasal septal button of FIG. 9 being installed in the irregular shaped septum hole.

Except for a utilization in the present invention of an elliptical shaped central portion 21, the nasal septal button 20 is similar to the nasal septum plug 13 in that it includes upper and lower disks 22 and 23, respectively, as shown in FIG. 9, that have flat inner faces 22a and 23a, respectively, and flat out faces 22b and 23b, respectively, that are also essentially parallel to one another. With the central portion length selected to provide for the inner faces 22a and 23a abutting against the septum surfaces at and adjacent to the septum hole or cavity 12, closing thereover. The nasal septal button 20, like the nasal septum plug 13, is also formed from a medically acceptable, human body compatible material, that needs to be flexible to allow for a bending of the disks or disk upon itself, as shown in FIG. 10. In which FIG. 10, a surgeon operator is shown squeezing the septal button between their fingers 24 and 25, and fitting the one disk 22 or 23 through the septum hole or cavity 12 to flex outwardly, returning to its original shape, after passage through the hole or cavity. A material known as medical grade silicone rubber and other flexible polymeric materials have been used successfully to form the nasal septal button 20, though, it should be understood, other like or similar human body compatible materials could be so used to manufacture the nasal septal button 20 of the invention within the scope of this disclosure.

In practice, as shown in FIG. 10, the surgeon operator compressed one or both of the nasal septal button 20 disks upon themselves, as shown in FIG. 1, and fits one disk 22 or 23 through the septum hole or cavity 12, such that the central portion 21 long or major axis C will fit within the long or major axis A of the hole or cavity 12. Which central portion 21 is formed to have a length to fit through the hole or cavity but will allow the disk 22 or 23 to pass therethrough and return to its original attitude and with the disks opposing surfaces 22a and 23a, respectively, to abut against the septum opposite surfaces, around the hole or cavity 12 edge, to close off and discourage air flow therethrough. The nasal septal button 20 is intended to remain in the patient's nose, closing off the septum hole or cavity 12, and accordingly, as set out above, needs to be formed from a medically acceptable material that is non-toxic, non-irritating, chemically inert and is sufficiently flexible to allow it to be installed, as set out above. While the above set out material is preferred for manufacture, other appropriate materials, such as polyethylene and polyketones, and the like, could be so used within the scope of this disclosure.

The invention in the nasal septal button 20 is shown herein as having a central portion 21 having, essentially a regular elliptical cross section. If should be understood, however, the central portion 21 cross section of the invention, within the scope of this disclosure, can be other than a regular ellipse so long as it has a pair of major and minor axis respectively, that will fit into and be maintained without turning in an irregular shaped hole or cavity 12. It should, however, be understood that the nasal septal button 20 can also be safely used in a septum hole or cavity that is circular. In such use, the central portion major axis will be the circular cavity diameter and though the nasal septal button 20 could potentially rotate somewhat in such circular hole or cavity, it will not travel along the hole or cavity during use, and the nasal septal button disks 22 and 23 will reliably close off the hole or cavity.

While a preferred form of my invention in a nasal septal button 20 has been shown and described herein, it should be understood that the present disclosure is made by way of example only and that variations are possible without departing from the subject matter coming within the scope of the following claims and a reasonable equivalency thereof, which subject matter I regard as my invention.

I claim:

1. A medical appliance for plugging a hole formed through a human patient's nasal septum comprising, a straight central portion of a length to extend through and is for disposition within a nasal septum hole, said central portion having a longer major axis than its minor axis, with the length of said major axis selected to fit within a longest axis of said nasal septum hole and said central portion is greater than the shortest axis of said nasal septum hole appliance for avoiding appliance rotation; a pair of disks that are each of a greater diameter than the central portion major axis, and with each said disk secured across a central portion opposite end; and said central portion and disks are formed as a single unit from a human body compatible, flexible material.

2. A medical appliance as recited in claim 1, wherein the central portion major axis is slightly less than the longest axis of the nasal septum hole; and the disks have the same diameter that is larger than the longest axis of said nasal septum hole, and said disks opposing surfaces are arranged to abut against opposite sides of said nasal septum, around said septum hole edge.

3. A medical appliance as recited in claim 1, wherein the central portion and disks are formed as a single unit from silicone rubber.

* * * * *